(12) United States Patent
Favreau et al.

(10) Patent No.: US 6,930,187 B2
(45) Date of Patent: Aug. 16, 2005

US006930187B2

(54) METHOD OF PREPARATION OF 21-AMINO EPOTHILONE DERIVATIVES

(75) Inventors: Denis Favreau, St. Hubert (CA); Joydeep Kant, Cherry Hill, NJ (US); Kathia Levesque, St-Catherine (CA); Shaopeng Wang, Glenview, IL (US); Zhengrong Guo, East Brunswick, NJ (US); Brian Leslie James, East Syracuse, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/365,892

(22) Filed: Feb. 13, 2003

(65) Prior Publication Data

US 2003/0187039 A1 Oct. 2, 2003

Related U.S. Application Data

(60) Provisional application No. 60/357,554, filed on Feb. 15, 2002.

(51) Int. Cl.[7] ............................................. C07D 417/06
(52) U.S. Cl. ...................... 548/204; 548/146; 548/203
(58) Field of Search ............................... 548/203, 204, 548/146

(56) References Cited

U.S. PATENT DOCUMENTS

| | | | | |
|---|---|---|---|---|
| 6,262,094 B1 | * | 7/2001 | Hoefle et al. | 514/365 |
| 6,291,684 B1 | | 9/2001 | Borzilleri et al. | |
| 6,300,355 B1 | | 10/2001 | Danishefsky et al. | |
| 6,380,227 B1 | * | 4/2002 | Mutz | 514/365 |
| 6,387,927 B1 | | 5/2002 | Altnamm et al. | |
| 6,399,638 B1 | | 6/2002 | Vite et al. | 514/366 |
| 6,489,314 B1 | * | 12/2002 | Ashley et al. | 514/183 |
| 6,531,497 B1 | | 3/2003 | Nicolaou et al. | |
| 6,589,968 B2 | * | 7/2003 | Arslanian et al. | 514/365 |
| 6,624,310 B1 | * | 9/2003 | Hoefle et al. | 548/204 |

FOREIGN PATENT DOCUMENTS

| | | |
|---|---|---|
| DE | 199 07 588 | 2/1999 |
| DE | 199 30 111 | 7/1999 |
| WO | WO 97/19086 | 5/1997 |
| WO | WO 98/22461 | 5/1998 |
| WO | WO 98/38192 | 9/1998 |
| WO | WO 00/39276 | 7/2000 |
| WO | WO 00/50423 | 8/2000 |

OTHER PUBLICATIONS

E. Nogales, Ann. Rev. Biochem., 2000, 69:277–302.
L. Wessjohann, Angew. Chem. Int. Ed. Engl. 1997, 36:715–718.
Höfle et al., Angew. Chem. Int. Ed. Engl., 1996, 35:1567–1569.
K.C. Nicolaou et al., Angew. Chem. Intl. Ed. Engl., 1998, 37:2014–2045.
G. Höfle et al., Angew. Chem. Int. Ed., 1999, 38:1971–1974.
G. Zuccarello et al., J. Org. Chem. 1998, 63:4898.
G. Gosselin et al., Nucleosides Nucleotides 1998, 17:1731.
K.C. Nicolaou et al., Angew. Chem., Int. Ed. Engl. 1998, 37:2708.
T. Honda et al., Heterocycles 1996, 42:109.
A.G. Schultz, H.A. Holoboski, M.S. Smyth, J. Am. Chem. Soc. 1996, 118:6210.
W.H. Pearson, J.V. Hines, J. Org. Chem. 1989, 54:4235.
U.S. Appl. No. 09/468,854.

* cited by examiner

*Primary Examiner*—Golam M M Shameem
(74) *Attorney, Agent, or Firm*—Deanna L. Baxam; Gary D. Greenblatt

(57) ABSTRACT

An improved method of synthesis of 21-amino epothilone derivatives which provides a one-pot conversion of 21-hydroxy epothilones to highly desirable 21-amino epothilones in high yield.

18 Claims, No Drawings

METHOD OF PREPARATION OF 21-AMINO EPOTHILONE DERIVATIVES

This application claims a benefit of priority from U.S. Provisional Application Ser. No. 60/357,554, filed Feb. 15, 2002, the entire disclosure of which is herein incorporated by reference.

FIELD OF THE INVENTION

The invention relates to the fields of organic synthesis, pharmaceutical process chemistry, and cancer chemotherapy. In particular, the inventive concept relates to an improved method of preparing 21-amino epothilone derivatives, which are useful in the treatment of a broad spectrum of tumors, including taxol-resistant tumors.

BACKGROUND OF THE INVENTION

Epothilones are macrocyclic lactones with useful antifungal and cytotoxic properties. Their action, as is the case with paclitaxel, is based on stabilization of microtubules, causing mitotic arrest in rapidly dividing cells and thus inhibition of the growth of tumors. For reviews, see E. Nogales, *Ann. Rev. Biochem.*, 2000, 69:277–302; L. Wessjohann, *Angew. Chem. Int. Ed. Engl.* 1997, 36:715–718; Höfle et al., *Angew. Chem. Int. Ed. Engl.*, 1996, 35:1567–1569; and K. C. Nicolaou et al., *Angew. Chem. Intl. Ed. Engl.*, 1998, 37:2014–2045. Typical epothilones, for example epothilones A, B, C, and D, carry a methylthiazolyl side chain, as shown below.

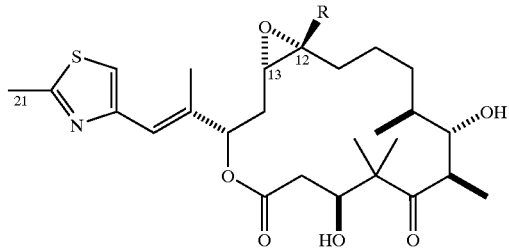

Epothilone A: R = H
Epothilone B: R = CH₃

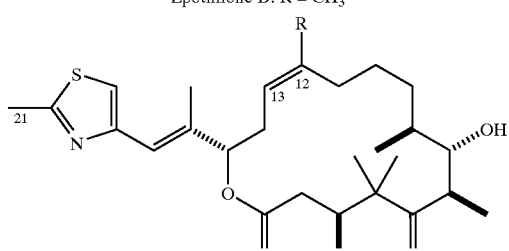

Epothilone C: R = H
Epothilone D: R = CH₃

Synthetic and semi-synthetic derivatives and analogues of epothilones have been described, in which carbon atoms 12 and 13 are variously derivatized via modification of the double bond or epoxide present in epothilones A, B, C, and D. Examples are found in U.S. Pat. No. 6,399,638, issued Jun. 4, 2002, which is commonly assigned with the present application and whose entire disclosure is incorporated herein by reference.

Functionalization of the C-21 position of epothilones has been accomplished via rearrangement of thiazole N-oxides, as described by G. Höfle et al., *Angew. Chem. Int. Ed.*, 1999, 38:1971–1974; and also in PCT international patent applications WO 98/22461 and WO 98/38192 (which are incorporated herein by reference). Alternatively, 21-hydroxy epothilones may be obtained by biotransformation (21-hydroxylation) of epothilones A–D with the aid of, for example, *Sorangium cellulosum* strains as described in WO 98/22461, or by *Actinomycetes* sp., e.g. strain SC15847 as described in WO 00/39276. The conversion of 21-hydroxy to 21-amino epothilones has been described by Höfle et al. in German patent applications DE 199 07 588 and DE 199 30 111, and in PCT international application WO 00/50423. These prior art methods utilize at least two steps, in contrast to the presently claimed invention.

The 21-amino epothilones and their derivatives are promising anti-tumor agents, however there are recognized difficulties associated with their production on a manufacturing scale. Because of the complexity of epothilone-like structures, advanced chemical intermediates must be prepared either by fermentation methods or by lengthy total syntheses, and these intermediates are accordingly expensive to produce. There remains a need, therefore, for shorter and higher-yielding processes for the preparation of 21-amino epothilones from such intermediates.

BRIEF DESCRIPTION OF THE INVENTION

The invention provides improved methods for synthesis of 21-amino epothilone derivatives, in which the prior art (DE 199 07 588, DE 199 30 111 and WO 00/50423) two-step conversion of a 21-hydroxy epothilone to a 21-amino epothilone is replaced by a one-pot process. The process generally comprises contacting a 21-hydroxy epothilone with an azide transfer agent and a suitable base, under conditions conducive to formation of the 21-azido epothilone, and conversion of the 21-azido group to a 21-amino group by reaction in situ with a reducing agent, followed by hydrolysis. The improved methods of the invention provide for a higher yield of 21-amino epothilones, and a considerable savings in time and cost of the conversion.

DETAILED DESCRIPTION OF THE INVENTION

The invention provides methods for the preparation of 21-amino epothilone derivatives of general formula (I):

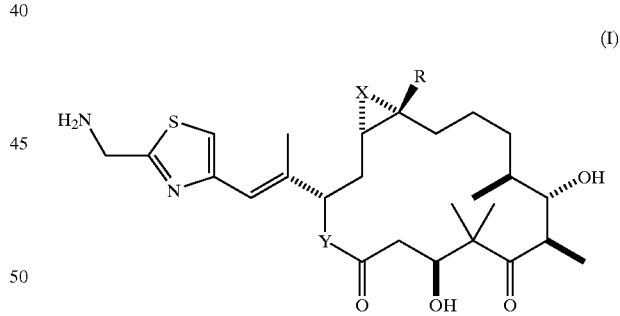

(I)

In formula (I), R is selected from the group consisting of H, alkyl, or substituted alkyl; X is selected from the group consisting of a carbon-carbon bond (as in epothilones C and D), O, S, CH₂, or NR'; Y is O or NH; R' is selected from the group consisting of H, alkyl, aryl, —CO—R'', —CO₂R''', CONHR'', CONR''R''', —SO₂R''', SO₂NHR'', and SO₂NR''R'''. R'' and R''' are independently selected from the group consisting of alkyl, aryl, aryl-alkyl, heteroaryl, and heteroaryl-alkyl, or R'' and R''' taken together with the nitrogen to which they are attached may comprise a nitrogen heterocycle, and additionally R'' may be H. Where X is a carbon-carbon bond, the 12,13-olefin may be of E or Z stereochemistry.

The preparation of the compounds of formula (I) may be carried out according to Scheme 1.

Scheme 1

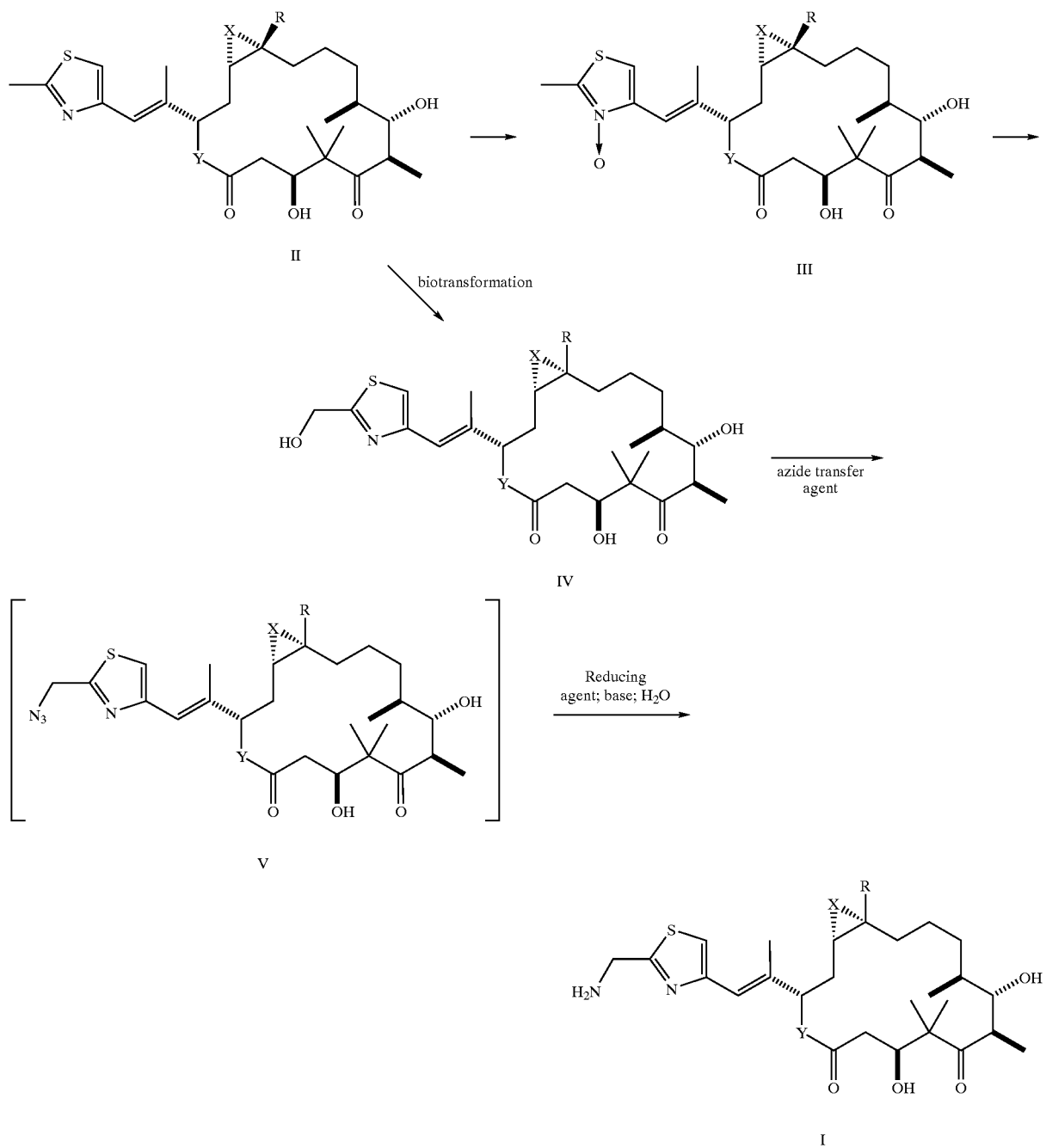

Starting from epothilones A–D, or from synthetic or semi-synthetic derivatives thereof, shown in Scheme 1 as formula (II), epothilone N-oxides of formula (III) can be obtained as described in the references cited above then converted to 21-OH epothilones of formula (IV). The epothilone starting material may optionally be purified by conventional means, for example by crystallization and/or chromatography, to minimize the proportion of impurities before being reacted to form the N-oxide.

One or both the 3-hydroxyl and 7-hydroxyl groups of the compound of formula (III) may optionally be protected, for example with trimethylsilyl groups or other trialkyl silyl groups, during formation of the N-oxide. Those skilled in the art will appreciate that it may also be advantageous or necessary to protect reactive functional groups in the moiety X, as appropriate (see, for example, WO 97/19086, the entire disclosure of which is herein incorporated by reference). Any other protecting means known in the art may also be employed for this purpose.

The N-oxide (formula III) is reacted with an acyl anhydride, preferably trifluoroacetic anhydride, in the presence of a hindered base such as collidine or 2,6-lutidine, to yield the 21-hydroxy epothilones IV after hydrolysis.

Scheme 2

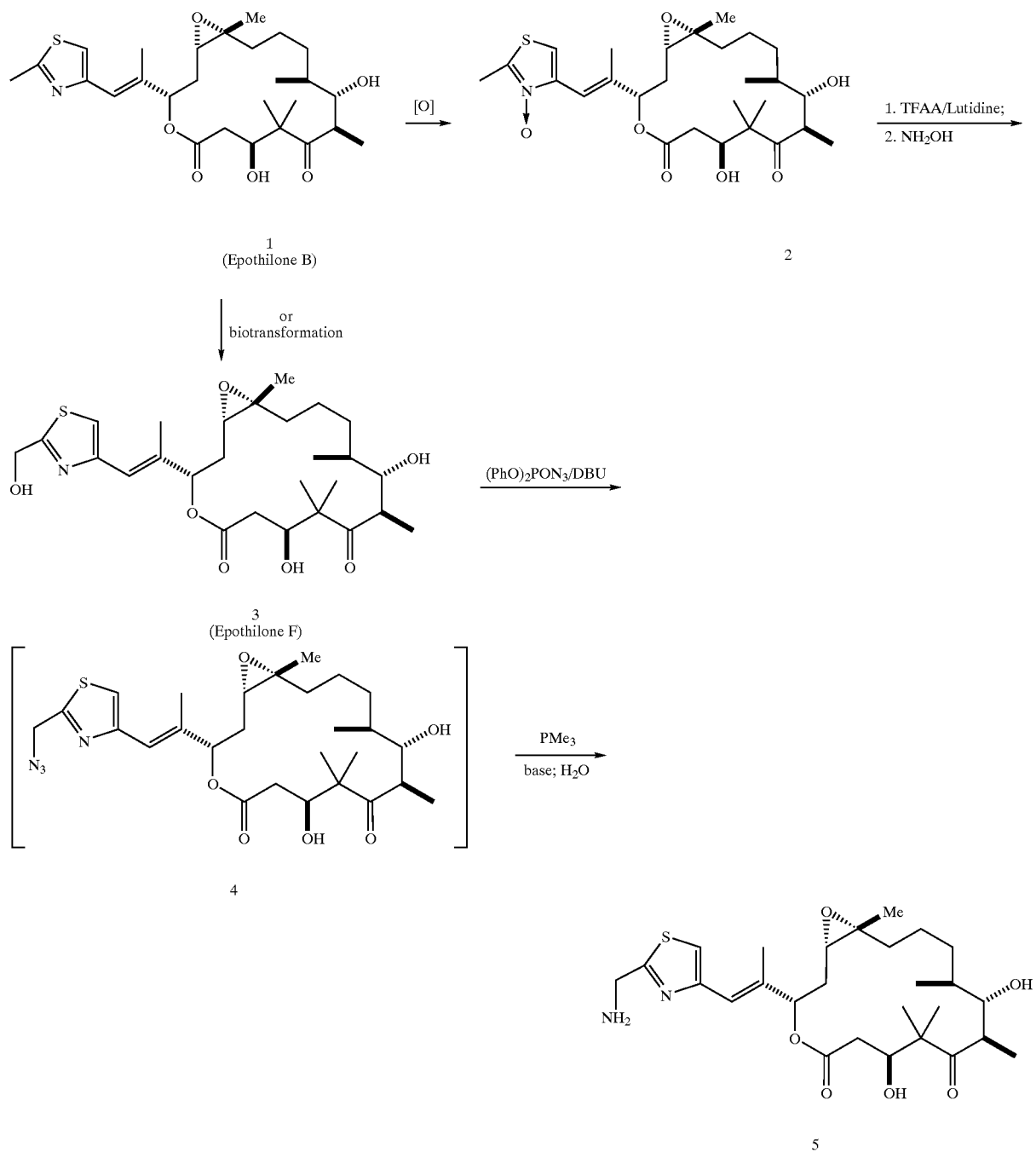

An exemplary process for preparing 21-amino epothilones via an N-oxide obtained from epothilone B is shown in the first two reaction steps of Scheme 2. The N-oxide of epothilone B, 2, is reacted to form epothilone F, 3, which is the starting material converted to an azido derivative, 4. The azido derivative is then reduced to form the 21-amino epothilone derivative, 5.

Generally, as shown in Scheme 1, the 21-hydroxy epothilones of formula (IV) may be obtained by oxidizing, then further reacting an epothilone starting material, which can be selected from epothilones A–D. Alternatively, the 21-hydroxy epothilones may be obtained by biotransformation (21-hydroxylation) of epothilones, e.g. epothilones A–D, with the aid of suitable microorganisms or with enzymes. Suitable microorganisms include, for example, *Sorangium cellulosum* strains as described in PCT Patent Application WO 98/22461, and *Actinomycetes* sp., e.g. strain SC 15847, as described in PCT Patent Application WO 00/39276. The entire disclosure of each of these applications is herein incorporated by reference in its entirety. Protected or unprotected epothilones such as those described in PCT Patent Application WO 97/19086) are appropriate and may be employed as the starting material in the method of the present invention. Synthetic or semi-synthetic epothilone starting materials may also be used.

In the presently claimed process, the conversion of a 21-hydroxy epothilone is accomplished, for example, using a phosphoryl azide, in the presence of a suitable base under conditions conducive to formation of the 21-azido epothilone. For examples of the use of phosphoryl azides in this manner, see: G. Zuccarello et al., *J. Org. Chem.* 1998, 63:4898; G. Gosselin et al., *Nucleosides Nucleotides* 1998, 17:1731; K. C. Nicolaou et al., *Angew. Chem., Int. Ed. Engl.* 1998, 37:2708; T. Honda et al., *Heterocycles* 1996, 42:109; A. G. Schultz, H. A. Holoboski, M. S. Smyth, *J. Am. Chem. Soc.* 1996, 118:6210; and W. H. Pearson, J. V. Hines, *J. Org. Chem.* 1989, 54:4235. Preferred phosphoryl azides are diaryl phosphoryl azides, and most preferred is diphenylphosphoryl azide. Any sufficiently polar and suitably inert organic solvent may be employed. The preferred solvent is tetrahydrofuran (THF). The presence of water or hydroxylic impurities in the solvent may consume a portion of the phosphoryl azide reagent; this may be overcome by addition of a compensating additional amount of phosphoryl azide and base. Most preferably the solvent is THF that is substantially free of water, for example commercial "anhydrous" grade THF or THF that has been dried over molecular sieves.

Suitable bases are strong hindered non-nucleophilic bases, such as for example 1,5-diazabicyclo[4.3.0]non-5-ene (DBN), 1,8-diazabicyclo[5.4.0]undec-7-ene (DBU), 1,5,7-triazabicyclo[4.4.0]dec-5-ene (TBD), 2,4,6-tri-tert-butylpyrimidine (TTBP), and diisopropylethylamine (DIPEA). Of such bases, DBU and DBN are preferred, and DBU is most preferred. In a preferred embodiment of the invention, the base is used in an excess amount relative to the molar equivalents of phosphoryl azide.

The 21-azido epothilone is then reacted with a reducing agent, followed by treatment with water, base or buffer to provide the 21-amino derivative. It is presumed that the conversion may proceed through an intermediate. In this respect, a strong reducing agent, for example a palladium catalyst such as Lindlar's catalyst, or an organophosphine reagent may be used. For example, this step may be performed by contacting the 21-azido epothilone of formula (V) with a trisubstituted phosphine. Suitable phosphines include trialkyl phosphines such as trimethyl phosphine, triethyl phosphine and tributyl phosphine; and triaryl phosphines such as triphenyl phosphine. Trimethyl phosphine is preferred.

Either of the foregoing alternative reducing steps may be performed without separation of the 21-azido compound from the reaction mixture obtained in the first step. Optionally, the solvent used in the azide formation may be removed, for example by evaporation, and replaced in part or entirely by a second solvent, but preferably the phosphine is added directly to the reaction mixture obtained in the azide formation step.

In an alternative embodiment of the invention, the base is added before the phosphine. This reverse addition may also be performed in situ, It should therefore be understood that within the scope of the present invention the order of addition of the phosphine reducing agent and the base may be reversed, with either variation of the process producing the desired compound of formula (I) in good yield.

As is reflected in Scheme 1, the process is completed by hydrolysis in conjunction with the reduction step. The hydrolysis may be effected by one of several means; for example by reaction with water, preferably in the presence of added acid or alkali, to obtain a 21-amino substituted compound of formula (I). In this embodiment, the hydrolysis is carried out with added alkali, the most preferred alkali being aqueous ammonium salts. A buffer may also be used instead of or in addition to the base. In particular, it has been observed that addition of the buffer further reduces impurities in the reaction end product. Suitable bases or buffers include, for example, $NH_4OH$, $NH_4Cl$, $NH_4Br$, $CF_3CO_2NH_4$, $NH_4OAc$, and mixtures thereof, e.g. aq. $NH_4OH/NH_4Cl$.

The process steps of the invention may be carried out at temperatures ranging from about 0° C. up to the boiling point of the solvent. They are preferably carried out between about 0° C. and about 40° C., and most preferably between about 20° C. and about 40° C.

Purification of the product preferably is achieved via chromatography and/or crystallization, though any suitable means of purification known in the art may also be used. Preferred crystallization solvents are mixtures of a polar solvent and a hydrocarbon, most preferably a mixture of ethyl acetate and heptane. The crude product is typically suspended in the solvent and mixed, if necessary with heating, before cooling. Optionally, the solution may be seeded during cooling to promote crystal formation.

The synthesis of the invention may be carried out as a batch or continuous process.

The following examples are provided to illustrate the present invention. However, it should be understood that the present invention is not limited to the examples herein described.

Conversion of (Epothilone B) to (Epothilone F)

EXAMPLE 1

Epothilone B (1.98 g, 3.90 mmol) was placed under argon and dissolved in 60 ml dry $CH_2Cl_2$. To this solution was added mCPBA (0.720 g, 4.17 mmol, 1.07 equivalents). The mixture was stirred at 25° C. for 5.5 hours. The reaction mixture was quenched with $NaHCO_3$ (60 ml), and extracted with $CHCl_3$ (3×75 ml). The organic phase was washed with water (100 ml) followed by 5% $Na_2SO_3$ (aq., 70 ml) and then brine (70 ml). The organic phase was then dried over $Na_2SO_4$. The crude reaction product was chromatographed using silica gel and eluted with 2% MeOH in $CHCl_3$ to yield the N-oxide (0.976 g, 48% yield) as a white solid.

(ii) To a resealable tube under argon was added the N-oxide (0.976 g, 1.86 mmol) dissolved in dry $CH_2Cl_2$ (35 ml), 2,6-lutidine (1.73 ml, 14.88 mmol, 8 equivalents) and $(CF_3CO)_2O$ (1.84 ml, 13.02 mmol, 7 equivalents). The tube was sealed and heated at 70° C. for 25 min. The mixture was allowed to cool and the solvent was removed under a stream of argon, followed by concentration to a few ml of dark yellow solution under vacuum. The reaction was diluted with MeOH (25 ml) and 28% $NH_4OH$ (aq., 2.9 ml) was added. The mixture was heated to 45° C. for 20 min, then cooled to room temperature. The crude product was concentrated on a rotary evaporator and chromatographed using silica gel, eluting with 4% MeOH in $CHCl_3$ to afford epothilone F (0.815 g, 84% yield).

EXAMPLE 2

Epothilone B (5.08 g, 10.0 mmol) was placed under argon and dissolved in dry $CH_2Cl_2$ (150 ml). To this solution was added powdered $NaHCO_3$ (2.11 g, 25.0 mmol, 2.5 equivalents) and purified mCPBA (4.31 g, 25.0 mmol, 2.5 equivalents). The mixture was stirred at 25° C. for 6 hours. The reaction mixture was washed with water (100 ml)

followed by 5% Na$_2$SO$_3$ (aq., 70 ml) and then brine (70 ml), and the organic phase was dried over Na$_2$SO$_4$. The crude reaction product was chromatographed on silica gel, eluting with 20–30% EtOAc/2% Et$_3$N/CH$_2$Cl$_2$, to afford the N-oxide (1.93 g., 36.8% yield) as a white fluffy solid. Larger-scale runs, employing 15 and 19 g of starting material, provided N-oxide epothilone B in yields of 39 and 32%, respectively.

The N-oxide (1.89 g, 3.60 mmol) was dissolved in dry CH$_2$Cl$_2$ (100 ml), 2,6-lutidine (3.15 ml, 27 mmol, 7.5 equivalents) and (CF$_3$CO)$_2$O (1.78 ml, 12.6 mmol, 3.5 equivalents). The mixture was stirred at 25° C. for 3 hours, then diluted with EtOH (60 ml), and the CH$_2$Cl$_2$ was removed under vacuum. The residue was cooled to 0° C., and 28% aqueous NH$_4$OH (0.73 ml, 6 equivalents) was added. The mixture was stirred at 0° C. for 2 hours, and then concentrated on a rotary evaporator and chromatographed on silica gel and eluted with 2% MeOH/0.2% Et$_3$N/CH$_2$Cl$_2$ to afford of epothilone F (0.95 g, 50% yield). Larger-scale runs, employing 6 and 6.42 g of starting material, also provided epothilone F in yields of 50%, with an additional 2 g of epothilone F present in mixed chromatographic fractions.

Comparative Examples—Multi-Step Synthesis

EXAMPLE 3

Preparation and Isolation of [1S-[1R*,3R*(E),7R*, 10S,11R*,12R*,16S*]]-3-[2-[2-(Azidomethyl)-4-thiazolyl]-1-methylethenyl]-7,11-dihydroxy-8,8,10, 12,16-pentamethyl-4,17-dioxabicyclo[14.1.0] heptadecane-5,9-dione

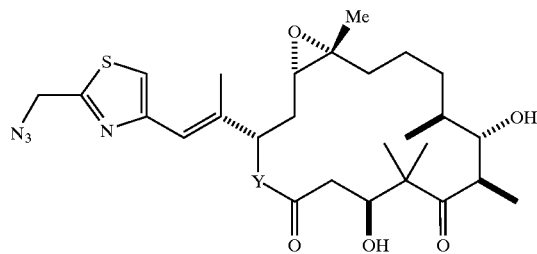

To a stirred solution of epothilone F (957 mg, 1.83 mmol) in tetrahydrofuran (20 ml) at 0° C. under argon was added diphenylphosphoryl azide (0.47 ml, 604 mg, 2.19 mmol, 1.2 equivalents). (Epothilone F can, for example, be obtained according to the process described in commonly assigned and co-pending U.S. patent application Ser. No. 09/468,854, the entire disclosure of which is incorporated herein by reference). The mixture was stirred for approximately 3 min. 1,8-diazabicyclo[5.4.0]undec-7-ene (0.27 ml, 278 mg, 1.83 mmol, 1 equivalents) was then added and the mixture was stirred at 0° C. After 2 hours, the mixture was warmed to 25° C. and stirred for 20 hours. The reaction mixture was diluted with ethyl acetate (150 ml) and washed with H$_2$O (50 ml). The aqueous layer was extracted with ethyl acetate (35 ml), and the combined organic layers were dried over Na$_2$SO$_4$ and concentrated under vacuum. The crude material was chromatographed using silica gel eluted with 50% ethyl acetate in hexanes to afford 21-azido-epothilone B (913 mg, 91% yield) as a clear, colorless oil. MS (ESI+): 549.3 (M+H)+; $^1$H-NMR (300 MHz, CDCl$_3$); δ=6.59 (bs, 17-H), 7.04 (s, 19-H), 4.63 (s, 21-H2); HRMS (DCl); C$_{27}$H$_{40}$N$_4$O$_6$S: [M+] calculated 549.2747, found 549.2768.

EXAMPLE 4

Preparation and Isolation of [1S-[1R*,3R*(E),7R*, 10S*,11R*,12R*,16S*]]-3-[2-[2-(Azidomethyl)-4-thiazolyl]-1-methylethenyl]-7,11-dihydroxy-8,8,10, 12,16-pentamethyl-4,17-dioxabicyclo[14.1.0] heptadecane-5,9-dione To a stirred solution of epothilone F (5 g, 9.55 mmol) in tetrahydrofuran (40.0 ml) at room temperature was added diphenylphosphoryl azide (2.28 ml, 2.89 g, 10.5 mmol, 1.1 equivalents). The mixture was stirred for approximately 5 min. 1,8-Diazabicyclo[5.4.0]undec-7-ene (1.72 ml, 1.74 g, 11.46 mmol, 1.2 equivalents) was then added. The mixture was heated to 40° C. and stirred for 3 hours. The reaction mixture was cooled to room temperature and diluted with ethyl acetate (160 ml), followed by washing with H$_2$O (25 ml). The organic layer was washed with 10% aqueous NH$_4$OH (25 ml), followed by 1M NH$_4$OH (25 ml). The combined aqueous layers were extracted with EtOAc (20 ml). The combined organic layers were washed with 15% aqueous NaH$_2$PO$_4$ (20 ml), dried over Na$_2$SO$_4$, and concentrated under vacuum to afford 21-azido-epothilone B (5.0 g. 95.4% yield) as a white solid.

EXAMPLE 5

Conversion to [1S-[1R*,3R*(E),7R*,10S,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a stirred solution of 21-azido-epothilone B (1.0 g, 1.82 mmol) in tetrahydrofuran (10.0 ml) was added trimethylphosphine (1 M in THF, 1.91 ml, 1.91 mmol, 1.05 equivalents) at room temperature. The mixture was stirred for 15 min. An aqueous solution of NH$_4$OH (1M, 1 ml) was added at room temperature. After the mixture was stirred at room temperature for 30 min, EtOAc (50 ml) and H$_2$O (10 ml) were added. The organic layer was washed with 5% aqueous NaH$_2$PO$_4$ (10 ml) and H$_2$O (10 ml). The organic phase was then dried over MgSO$_4$ and the solvents were removed under vacuum to yield 21-amino epothilone B (0.81 g, 85% yield) as a slightly pink solid.

Preparation of 21-Amino Epothilone Derivatives

EXAMPLE 6

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a stirred suspension of epothilone F (10 g, 19.1 mmol) in tetrahydrofuran (200 ml) under argon, chilled in an ice bath to 5° C. or below, was added diphenylphosphoryl azide (6.20 ml, 7.90 g, 28.6 mmol, 1.5 equivalents). The mixture was stirred for approximately 10 min. 1,8-diazabicyclo [5.4.0]undec-7-ene (3.43 ml, 3.53 g, 22.8 mmol, 1.2 equivalents) was then added gradually at a rate that maintained the temperature of the mixture below 8° C. The mixture was stirred for 30 min., then allowed to warm to 20° C. and stirred for 18 hours. To the reaction mixture was added a solution of 1.0 M trimethylphosphine in tetrahydrofuran (21 ml, 18.3 g, 21 mmol, 1.1 equivalents), which generated a mild exotherm with gas evolution. The mixture was allowed to stir at 20° C. for 30 minutes, and water (52 ml) was added. After 30 minutes, 28% aqueous NH$_4$OH (26.5 ml) was added. After stirring at 25° C. for another 30 minutes, water (100 ml) was added, and the mixture was extracted with methylene chloride (3×100 ml). The combined organic extracts were washed with 1.0 M aqueous ammonium hydroxide (2×100 ml), and then with half-saturated aqueous sodium chloride (100 ml). The solvents were removed on a rotary evaporator, and the residue dried in vacuo for 18 hours.

The crude material from several synthetic runs (from 36 g starting material in total) was chromatographed on silica gel (810 g, density 0.45 g/ml; 1800 ml), and eluted with 0.2% Et$_3$N, 2.5% MeOH in CH$_2$Cl$_2$, to yield 21-amino epothilone B (27.1 g) as a white solid. MS (ESI+): 523.3 (M+H)$^+$. An additional 2.37 g was obtained by re-chromatography of later mixed fractions, for a total of 29.5 g (82.4% yield).

The material was dissolved in CH$_2$Cl$_2$, (200 ml) and the solution filtered through a 0.45 micron membrane (Durapore™ HVHP, Millipore Inc., Bedford Mass.) and evaporated to dryness in vacuo. Crystallization was carried out by dissolving the residue in ethyl acetate (344 ml) at 75° C., slowly adding cyclohexane (688 ml), and slowly cooling with stirring and with addition of seed crystals of 21-amino epothilone B. The mixture was held with stirring at 40° C. for an hour, then allowed to cool further to room temperature and stirred for 12 hours. The mixture was then cooled to below 5° C. in an ice bath, stirred for 4 hours at 0 to 5° C., and filtered. The solids were rinsed with ice-cold 10% ethyl acetate in cyclohexane (3×30 ml) and then dried in vacuo at 40° C. for 18 hours to provide crystalline 21-amino epothilone B (27 g, 75% overall yield) as white plates.

EXAMPLE 7

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione THF was dried over 3A molecular sieves prior to use. To a stirred suspension of epothilone F (10 g, 19.1 mmol) in dry tetrahydrofuran (200 ml) under argon, was added diphenylphosphoryl azide (6.20 ml, 7.90 g, 28.6 mmol, 1.5 equivalents). The mixture was stirred for about 10 min. 1,8-diazabicyclo[5.4.0]undec-7-ene (3.43 ml, 3.53 g, 22.8 mmol, 1.2 equivalents) was added gradually, at a rate that maintained the temperature of the mixture below 30° C. The mixture was stirred for 12 to 24 hours (overnight). To the reaction mixture was added a solution of 1.0 M trimethylphosphine in tetrahydrofuran (21 ml, 18.3 g, 21.04 mmol, 1.1 equivalents), at a rate that maintained the temperature of the mixture below 27° C. The mixture was stirred at room temperature for 30 minutes, and water (52 ml) was added. After 30 minutes, 28% aqueous NH$_4$OH (26.5 ml) was added, and the mixture stirred for 30 minutes. Water (100 ml) was added, and the mixture was extracted with methylene chloride (3×100 ml). The combined organic extracts were washed with 1.0M aqueous ammonium hydroxide (2×100 ml). NMR analysis was used to determine the presence of residual diphenylphosphate in the organic phase, and an additional wash with 1.0 M aqueous ammonium hydroxide (100 ml) was carried out. The organic phase was then washed with half-saturated aqueous sodium chloride (100 ml), the solvents were removed on a rotary evaporator, and the residual solid was dried in vacuo for 18 hours. The crude product was purified within 24 hours, or stored at –15° C. or below.

The crude material was purified by chromatography and recrystallization as described in Example 6.

EXAMPLE 8

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a stirred suspension of epothilone F (47.12 g, 90.0 mmol) in tetrahydrofuran (942 ml, previously dried over 3A molecular sieves) under argon, was added diphenylphosphoryl azide (29.2 ml, 37.3 g, 135.5 mmol, 1.5 equivalents). The mixture was stirred for about 10 min. 1,8-diazabicyclo [5.4.0]undec-7-ene (24.5 ml, 24.94 g, 163.8 mmol, 1.8 equivalents) was then added gradually, at a rate that maintained the temperature of the mixture below 30° C. The mixture was stirred for 22 hours. To the reaction mixture was added a solution of trimethylphosphine in tetrahydrofuran (1.0 M, 99.0 ml, 86.3 g, 99.0 mmol, 1.1 equivalents), at a rate that maintained the temperature of the mixture below 30° C. The mixture was stirred at room temperature for 30 minutes, and water (244 ml) was added. After 30 minutes, 28% aqueous NH$_4$OH (125.0 ml) was added, and the mixture stirred for 30 minutes. Water (470 ml) was added, and the mixture was extracted with methylene chloride (3×100 ml). The combined organic extracts were washed with aqueous ammonium hydroxide (1.0 M, 3×470 ml). NMR analysis was used to determine the presence of residual diphenylphosphate in the organic phase. The organic phase was then washed with half-saturated aqueous sodium chloride (470 ml), the solvents were removed on a rotary evaporator, and the residual solid was dried in vacuo for 18 hours to afford the crude product (56.72 g, 120.6% yield).

The crude product was purified by column chromatography using silica gel pre-treated with 2.5% methanol-0.2% triethylamine-dichloromethane. The chromatographed material was dissolved in CH$_2$Cl$_2$, and the solution filtered through a 0.45 micron membrane (Durapore™ HVHP, Millipore Inc., Bedford Mass.) and evaporated to dryness. To the purified product (30.6 g) was added ethyl acetate (370 mL), the resulting suspension was heated at 72–75° C. to obtain a solution and n-heptane (370 mL) added slowly. The mixture was treated with seeds (622 mg) and then held with stirring at 72° C. for 1 hr. The suspension is then allowed to cool slowly and stirred at 15–25° C. for 18 hrs. After cooling at +5° C., the resulting solid was isolated by filtration, washed with 10% ethyl acetate in heptane (93 mL in three portions) followed by vacuum drying at 50–60° C. to afford the crystalline 21-amino epothilone (28.93 g, 67.6% yield corrected for input potency).

EXAMPLE 9

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a suspension of epothilone F (334 g, 637.8 mmol) and diphenylphosphoryl azide (208 ml, 264.3 g, 960 mmol, 1.5 eq) in tetrahydrofuran (6680 ml, previously dried over 3A molecular sieves) was added gradually 1,8-diazabicyclo [5.4.0]undec-7-ene (DBU, 172 ml, 175 g, 1.15 mol, 1.8 eq) and the reaction subsequently stirred at 15–25° C. for 6–18 hrs. To the reaction mixture was then added a 2.4M solution of ammonium hydroxide (2600 ml, 10 eq ), followed by slow addition of a 1.0 M trimethylphosphine/tetrahydrofuran solution (700 ml, 1.1 eq), and the mixture stirred for 1 hr. The reaction mixture was diluted with water (3340 ml) and the aqueous phase extracted with dichloromethane (3×3340 ml). The organic phase was then washed with diluted ammonium hydroxide (10,710 ml in five portions) and half saturated sodium chloride solutions (3340 ml in two portions); the dichloromethane solution was partially concentrated under reduced pressure to ca 1670 ml. Ethyl acetate (3340 ml) was then added and the mixture reconcentrated to 1670 ml. The process was repeated and to the mixture was added n-heptane (5010 ml). The resulting suspension was stirred for 1 hr and the solid isolated by filtration followed by vacuum drying at 50–60C. to afford the crude product (305.2 g, 91.4% yield).

The crude product from two reactions (136.0 and 334.0 g input) was purified by column chromatography using silica gel pre-treated with 2.5% methanol-0.2% triethylamine-dichloromethane, or optionally with 5% methanol-ethyl acetate. The chromatographed material (340 g) was dissolved in $CH_2Cl_2$, and the solution filtered through a 0.45 micron membrane (Durapore™ HVHP, Millipore Inc., Bedford Mass.) and evaporated to dryness. To the purified product (339.10 g) was added ethyl acetate (4070 ml), the resulting suspension was heated at 72–75° C. to obtain a solution and n-heptane (4070 ml) added slowly. The mixture was allowed to cool slowly in the presence of seeds and stirred at 15–25° C. After cooling at +5° C., the resulting solid was isolated by filtration, washed with of heptane (1020 ml in three portions) followed by vacuum drying to afford crystalline 21-amino epothilone (317.7 g, 73.4% yield corrected for input potency). (Optionally, the product can also be recrystallized from ethyl acetate-heptane to improve quality.)

EXAMPLE 10

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a stirred suspension of epothilone F (2.5 g, 4.77 mmol, 86.2% potency) in tetrahydrofuran (25 ml) was added diphenylphosphoryl azide (1.14 ml, 1.45 g, 5.25 mmol, 1.1 equivalents) at room temperature. The mixture was stirred for approximately 5 min. 1,8-Diazabicyclo[5.4.0]undec-7-ene (0.86 ml, 0.87 g, 5.73 mmol, 1.2 equivalents) was then added over 10 min. The mixture was stirred for 10 min, and then allowed to warm to 40° C. and stirred for 3 hours. The mixture was cooled to 30° C., and a mixture of aqueous solution of $NH_4Cl$ (2M, 2.5 ml) and $NH_4OH$ (2M, 2.5 ml) was added. After the mixture was stirred for 10 min at 30° C., trimethylphosphine (1M in tetrahydrofuran, 5.01 ml, 5.01 mmol, 1.05 equivalents) was added over 10 min. The mixture was allowed to stir at 30° C. for 3 hours and then at room temperature for 15 hours. EtOAc (100 ml) and aqueous $NH_4OH$ (1 M, 20 ml) were added. The organic layer was washed with aqueous $NH_4OH$ (1 M, 20 ml). The combined aqueous layers were extracted with EtOAc (20 ml). The combined organic layers were washed with $H_2O$ (20 ml) and dried over $MgSO_4$. The solvents were removed on a rotary evaporator, and the residue dried in vacuo to provide the crude 21-amino epothilone B (2.45 g) as an off-white solid. The crude 21-amino epothilone B (2.45 g) was crystallized from EtOAc/heptane to give 21-amino epothilone B (1.86 g, 86.5% yield corrected for input potency) as a white solid.

EXAMPLE 11

[1S-[1R*,3R*(E),7R*,10S*,11R*,12R*,16S*]]-3-[2-[2-(Aminomethyl-4-thiazolyl]-1-methylethenyl]-7,11-dihydroxy-8,8,10,12,16-pentamethyl-4,17-dioxabicyclo[14.1.0]heptadecane-5,9-dione To a stirred suspension of epothilone F (2.5 g, 4.77 mmol, 86.2% potency) in tetrahydrofuran (25 ml) was added diphenylphosphoryl azide (1.14 ml, 1.45 g, 5.25 mmol, 1.1 equivalents) at room temperature. The mixture was stirred for approximately 5 min. 1,8-diazabicyclo[5.4.0]undec-7-ene (0.86 ml, 0.87 g, 5.73 mmol, 1.2 equivalents) was then added over 10 min. The mixture was stirred for 10 min. and then allowed to warm to 35° C. and stirred for 6.5 hours. The mixture was cooled to 10° C., and a mixture of aqueous solution of $NH_4Br$ (2M, 5 ml) and $NH_4OH$ (2M, 5 ml) was added. After the mixture was stirred for 5 min, trimethylphosphine (1M in tetrahydrofuran, 5.01 ml, 5.01 mmol, 1.05 equivalents) was added over 10 min at 10° C. The mixture was allowed to stir at 35° C. for 4 hours and then cooled to room temperature. EtOAc (80 ml) and aqueous $NH_4OH$ (1 M, 10 ml) were added. The organic layer was washed with aqueous $NH_4OH$ (1 M, 20 ml). The combined aqueous layers were extracted with EtOAc (20 ml). The combined organic layers were washed with $H_2O$ (20 ml) and dried over $MgSO_4$. The solvents were removed on a rotary evaporator, and the residue dried in vacuo to provide the crude 21-amino epothilone B (2.5 g) as an off-white solid. The crude 21-amino epothilone B (2.45 g) was crystallized from EtOAc/heptane to give 21-amino epothilone B (1.95 g, 90% yield corrected for input potency) as a white solid.

EXAMPLE 12

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a stirred suspension of epothilone F (5.0 g, 9.55 mmol, 86.2% potency) in tetrahydrofuran (50 ml) was added diphenylphosphoryl azide (2.28 ml, 2.89 g, 10.5 mmol, 1.1 equivalents) at room temperature. 1,8-Diazabicyclo[5.4.0] undec-7-ene (1.73 ml, 1.74 g, 11.46 mmol, 1.2 equivalents) was then added over 10 min. The mixture was stirred for 10 min. and then allowed to warm to 35° C. and stirred for 6.5 hours. The mixture was cooled to 20° C., and a mixture of aqueous solution of $CF_3COONH_4$ (4M, 10 ml) and $NH_4OH$ (4M, 10 ml) was added. After the mixture was stirred for 5 min, trimethylphosphine (1M in tetrahydrofuran, 10.03 ml, 10.03 mmol, 1.05 equivalents) was added over 10 min at 20° C. The mixture was allowed to stir at 35° C. for 2 hours and then at 5° C. for 14 hours. EtOAc (200 ml) and aqueous $NH_4OH$ (1 M, 10 ml) were added. The organic layer was washed with aqueous $NH_4OH$ (1 M, 30 ml). The combined aqueous layers were extracted with EtOAc (2×30 ml). The combined organic layers were washed with a mixture of brine (20 ml) and $H_2O$ (20 ml). The solvents were removed to yield ~60 ml on a rotary evaporator, and EtOAc (60 ml) was added. The solvent was removed again to ~65 ml, and the resulting slurry was crystallized from EtOAc/heptane to give 21-amino epothilone B (3.75 g, 87% yield corrected for input potency) as a white solid.

EXAMPLE 13

Synthesis of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione To a suspension of epothilone F (5.0 g, 9.55 mmol, 86.2% potency) and diphenylphosphoryl azide (2.27 ml, 10.5 mmol, 1.1 eq) in tetrahydrofuran (40 ml) was added gradually 1,8-diazabicyclo[5.4.0]undec-7-ene (DBU, 1.71 ml, 11.46 mmol, 1.2 eq) and the reaction subsequently stirred at 25–40° C. for 4–6 hrs. To the reaction mixture was then added a 6.0 M solution of ammonium acetate (7.96 ml, 47.7 mmol, 5 eq) followed by 1.0 M trimethylphosphine/tetrahydrofuran solution (1.5 eq). The reaction mixture was diluted with water and the aqueous phase extracted with three portions of ethyl acetate (40 ml each). The organic phase was then washed with three portions of diluted ammonium hydroxide (40 ml each). The combined aqueous washes are then extracted with two portions of ethyl acetate (40 ml each). The combined ethyl acetate phases are washed with two portions of water (20 ml each) then concentrated and azeotropically dried under reduced pressure to a final volume of 60 ml. The resulting solution was heated at 65–75° C. and 70 ml n-heptane was added slowly. The mixture was allowed to cool slowly and stirred at a final temperature of 15–20° C. The resulting solid (3.34 g, 78% corrected for input potency) was isolated by filtration followed by vacuum drying to afford crystalline product.

We claim:

1. A one-pot method for the preparation of 21-amino epothilone derivatives of formula (I)

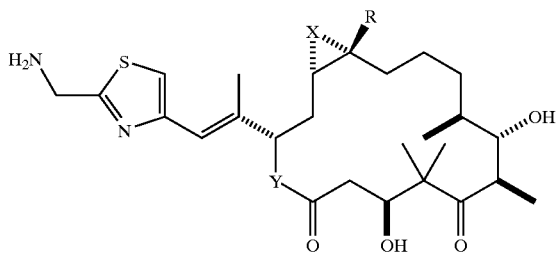

(I)

wherein R is selected from the group consisting of H, alkyl, or substituted alkyl; X is selected from the group consisting of a carbon-carbon bond, O, S, $CH_2$; Y is O; comprising, in situ, the steps of (a) contacting a 21-hydroxy epothilone derivative of formula (IV)

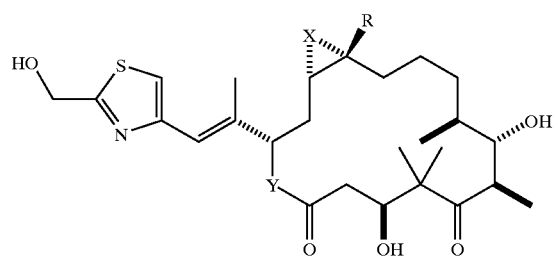

IV with an azido transfer agent to form a 21-azido epothilone of formula (V);

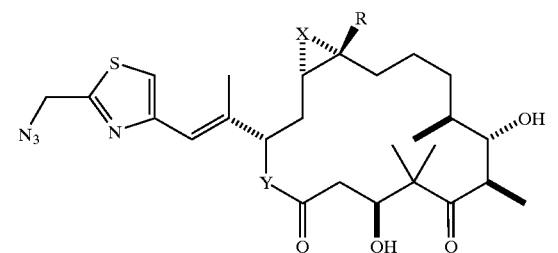

(V)

and (b) contacting the 21-azido epothilone with a reducing agent to form a 21-amino epothilone derivative according to formula (I).

2. The method of claim 1 further comprising:
a) reacting an epothilone starting material with an oxidizing agent; or
b) converting an epothilone starting material by biotransformation;
to obtain a 21-hydroxy epothilone derivative according to formula (IV), then reacting the compound of formula (IV), in situ, with the azido transfer agent according to step (a) to form a compound of formula (V).

3. The method of claim 2 wherein the biotransformation is performed using an enzyme derived from a microorganism selected from a strain of a *Sorangium cellulosum* or *Actinomycetes* species.

4. The method of claim 2 wherein the biotransformation is performed using an enzyme derived from a microorganism selected from a strain of a *Sorangium cellulosum* or *Actinomycetes* species.

5. The method of claim 1 wherein the reducing agent is a palladium catalyst or an organophosphine reagent.

6. The method of claim 5, wherein the reducing agent is a trialkyl phosphine and the azido transfer agent is a dialkyl phosphoryl azide.

7. The method of claim 2 wherein the oxidizing agent is 3-chloroperoxybenzoic acid.

8. The method of claim 1 wherein the reaction of step (a) is carried out in the presence of a non-nucleophilic base.

9. The method of claim 1 wherein the reaction of step (b) is carried out in the presence of a water, a base, a buffer, or combination thereof.

10. The method of claim 8 wherein the non-nucleophilic base is selected from the group consisting of 1,5-diazabicyclo[4.3.0]non-5-ene, 1,8-diazabicyclo[5.4.0]undec-7-ene, 1,5,7-triazabicyclo[4.4.0]dec-5-ene (TBD), 2,4,6-tri-tert-butylpyrimidine and diisopropylethylamine.

11. The method of claim 9 wherein the base is selected from the group consisting of ammonium hydroxide, ammonium salts or water, and the buffer is selected from the group consisting of mixtures thereof.

12. The method of claim 1 further comprising removal of excess solvent to provide a dried product containing a 21-amino epothilone derivative according to formula (I).

13. The method of claim 12 further comprising purifying the 21-amino epothilone derivative by crystallization from an organic solvent.

14. The method of claim 12 further comprising purifying the 21-amino epothilone derivative by chromatography.

15. The method of claim 2 wherein the epothilone starting material is a compound of formula (II)

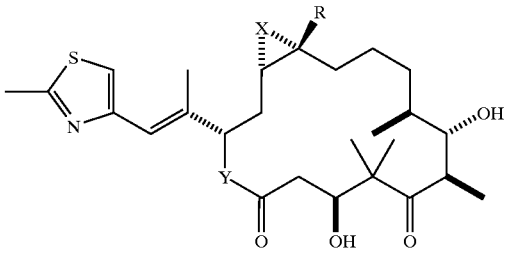

II wherein R, Y, and X are as defined in claim 1.

16. The method of claim 15 wherein each of X and Y is O, and R is H or methyl.

17. The method of claim 16 wherein the compound of formula (II) is converted by biotransformation using a microorganism selected from a strain of a *Sorangium cellulosum* or *Actinomycetes* species.

18. The method of claim 17 wherein the compound of formula (II) is converted by biotransformation using an enzyme derived from a microorganism selected from a strain of a *Sorangium cellulosum* or *Actinomycetes* species.

* * * * *

UNITED STATES PATENT AND TRADEMARK OFFICE
CERTIFICATE OF CORRECTION

PATENT NO. : 6,930,187 B2  
APPLICATION NO. : 10/365892  
DATED : August 16, 2005  
INVENTOR(S) : Favreau et al.

Page 1 of 1

It is certified that error appears in the above-identified patent and that said Letters Patent is hereby corrected as shown below:

Column 15:
  Lines 32-34, "wherein R is selected from the group consisting of H, alkyl or substituted alkyl; X is selected from the group consisting of carbon-carbon bond, O, S, $CH_2$;" should read:

--wherein R is selected from the group consisting of H, alkyl and substituted alkyl; X is selected from the group consisting of carbon-carbon bond, O, S, and $CH_2$;--

Column 16:
  Lines 39-41, "11. The method of claim 9 wherein the base is selected from the group consisting of ammonium hydroxide, ammonium salts or water," should read:

--11. The method of claim 9 wherein the base is selected from the group consisting of ammonium hydroxide, ammonium salts, and water,--

Signed and Sealed this

Twenty-ninth Day of August, 2006

JON W. DUDAS  
*Director of the United States Patent and Trademark Office*